US 6,628,977 B2

(12) United States Patent
Graumann et al.

(10) Patent No.: US 6,628,977 B2
(45) Date of Patent: Sep. 30, 2003

(54) METHOD AND SYSTEM FOR VISUALIZING AN OBJECT

(75) Inventors: Rainer Graumann, Hoechstadt (DE); Norbert Rahn, Forchheim (DE); Siegfried Wach, Hoechstadt (DE)

(73) Assignee: Siemens Aktiengesellschaft, Munich (DE)

( * ) Notice: Subject to any disclaimer, the term of this patent is extended or adjusted under 35 U.S.C. 154(b) by 233 days.

(21) Appl. No.: 09/748,320

(22) Filed: Dec. 22, 2000

(65) Prior Publication Data
US 2001/0029334 A1 Oct. 11, 2001

(30) Foreign Application Priority Data

Dec. 28, 1999 (DE) .......................... 199 63 440

(51) Int. Cl.[7] ................................. A61B 5/05
(52) U.S. Cl. ..................................... 600/407
(58) Field of Search ................. 600/407, 408, 600/409, 410, 1; 250/363.01; 606/2, 20, 27, 32

(56) References Cited

U.S. PATENT DOCUMENTS

| 4,791,934 A | * | 12/1988 | Brunnett ....................... 600/429 |
| 4,821,727 A | * | 4/1989 | Levene et al. ................. 600/407 |
| 4,955,046 A | * | 9/1990 | Siczek et al. ................. 378/197 |
| 5,227,969 A | * | 7/1993 | Waggener et al. ........... 600/431 |
| 5,287,546 A | * | 2/1994 | Tesic et al. ................... 378/54 |
| 5,828,774 A | * | 10/1998 | Wang .......................... 382/128 |
| 5,852,646 A | | 12/1998 | Klotz et al. |
| 6,201,983 B1 | * | 3/2001 | Haumann et al. ............ 600/407 |
| 6,296,613 B1 | * | 10/2001 | Emmenegger et al. ....... 600/459 |
| 6,434,262 B2 | * | 8/2002 | Wang .......................... 382/132 |
| 6,485,413 B1 | * | 11/2002 | Boppart et al. .............. 600/160 |
| 6,490,467 B1 | * | 12/2002 | Bucholz et al. .............. 600/407 |

FOREIGN PATENT DOCUMENTS

DE    OS 19807884    2/1998

OTHER PUBLICATIONS

"Medical Instrumentation Application and Design," 3rd Ed., Webster, Ed. (1998) pp. 540–543.

* cited by examiner

Primary Examiner—Daniel Robinson
(74) Attorney, Agent, or Firm—Schiff Hardin & Waite

(57) ABSTRACT

In a method and a system for visualizing the position and orientation of an object that is penetrating, or that has penetrated, into a subject, a first set of image data are produced from the interior of the subject before the object has penetrated into the subject, a second set of image data are produced from the interior of the subject during or after the penetration of the object into the subject, the sets of image data are connected and are superimposed to form a fused set of image data, and an image obtained from the fused set of image data is displayed. The system has an x-ray computed tomography apparatus, and an x-ray apparatus, and/or an ultrasound apparatus for producing the first and second sets of data, respectively.

21 Claims, 2 Drawing Sheets

METHOD AND SYSTEM FOR VISUALIZING AN OBJECT

BACKGROUND OF THE INVENTION

1. Field of the Invention

The present invention relates to a method and to a system for visualizing the position and orientation of an object that is penetrating or has penetrated a subject.

2. Description of the Prior Art

In many technical applications, the problem occurs of making an object visible that has penetrated into a subject and is thus no longer visible, or is only partly visible, with respect to its position and orientation in the subject, e.g., for a person handling the object. In medical technology there is, for example, a problem of this sort in the removal of tissue from inside the body of a living being, using a biopsy needle that is to be guided by a physician to the point of the tissue to be examined in a manner that is as precise and closely monitored as possible. As a rule, guidance of the biopsy needle is accomplished using an imaging system, for example an x-ray computed tomography apparatus, a C-arm x-ray apparatus, or an ultrasound apparatus, with which images can be obtained from inside the body of the living subject, these images indicating the position and orientation of the biopsy needle relative to the tissue to be examined.

Advantages of the use of an x-ray computed tomography apparatus as an imaging system in the biopsy procedure are that in the visualization of the biopsy needle ensues in real time, and that good presentation of soft tissue parts occurs in images obtained using an x-ray computed tomography apparatus. In this way, the current position of the biopsy needle relative to the tissue to be examined can be visualized and measured. In addition, in the obtained images not only deformations of the biopsy needle during penetration into the body of the living being, but also pathological and anatomical characteristics of the imaged tissue, can for the most part be recognized clearly. A disadvantage in the use of an x-ray computed tomography apparatus is the relatively small diameter of the gantry opening, which does not present an optimal operating field for the execution of a biopsy procedure. Since in addition the hands of the physician carrying out the biopsy procedure are located within the x-ray projection fan of the x-ray computed tomography apparatus during the biopsy procedure, the physician is exposed to a significant radiation load.

The use of an x-ray apparatus, in particular a C-arm x-ray apparatus, as an imaging system for a biopsy procedure has the advantage that the radiation load for the physician guiding the biopsy needle is significantly less than in a biopsy procedure employing an x-ray computed tomography apparatus. In addition, more space is available for the biopsy procedure. Moreover, obtaining x-ray images using a C-arm x-ray apparatus is generally more economical than is the case with an x-ray computed tomography apparatus. A disadvantage of the x-ray images obtained using a C-arm x-ray apparatus is the two-dimensional representation—which is often insufficient—of the tissue to be examined, and the fact that tumors in x-ray images of this sort are often insufficiently recognizable or not recognizable at all.

Advantages of the use of ultrasound for imaging in the biopsy procedure are that the exposure method free of radiation load, and that the images are obtained in real time. However, a disadvantage is that the tissue to be examined cannot always be represented in ultrasound images. Problems in such imaging always result when media that cannot be penetrated by ultrasound, or can be penetrated by ultrasound only with difficulty, for example air or bone, are located between the ultrasound sending and receiving surfaces of the ultrasound apparatus and the tissue to be examined.

In order to compensate for the disadvantages of the individual imaging systems, it is known to obtain x-ray images in multiple exposures during the execution of a biopsy procedure, using a C-arm x-ray system and an x-ray computed tomography apparatus. However, the patient must be moved from one bed to another numerous times for the exposures using the C-arm x-ray apparatus and for the exposures using the x-ray computed tomography apparatus, which makes the execution of the biopsy procedure expensive and complicated. A further technological development involves the use of what are known as "sliding gantries," which refers to a coupling of an x-ray computed tomography apparatus with a C-arm x-ray apparatus. A patient bed supporting a patient can thereby be moved back and forth between the x-ray computed tomography apparatus and the C-arm x-ray apparatus for different diagnostic exposures without repositioning the patient.

In spite of this improvement, the execution of a biopsy procedure proves to be laborious due to the required movement back and forth of the patient between two imaging systems during a biopsy procedure.

German OS 198 07 884 discloses a method and an apparatus for obtaining intraoperative exposures of a subject under examination which are compared with exposures that are produced pre-operatively and/or intraoperatively.

In German OS 196 20 371, a method and an arrangement are disclosed in which, for example before a biopsy, a series of two-dimensional x-ray exposures are produced of a subject under examination, in particular to produce contrast-rich x-ray exposures of vascular structures using an imaging apparatus. Using a second imaging apparatus, a volume data set of the subject under examination is produced, from which a series of two-dimensional projections are generated, which visualize, in particular, contrast-rich structures of the subject under examination. Subsequently, the projections and the two-dimensional x-ray images are superposed to form a series of superposition images.

SUMMARY OF THE INVENTION

An object of the present invention is to provide a method and a system of the type described above wherein the visualization of an object that has penetrated into a subject is simplified.

According to the invention, this object is achieved in a method for visualizing the position and orientation of an object that is penetrating or has penetrated into a subject, wherein a first set of image data is produced from the interior of the subject, using a first apparatus for recording image data, before the object has penetrated into the subject, a second set of image data is produced from the interior of the subject, using a second apparatus, realized differently from the first apparatus, for recording image data while the object penetrates into the subject, or after the object has penetrated into the subject, a connection (linking relationship) between the image data of the first set and the image data of the second set is produced, image data of the first set are superimposed with image data of the second set in order to form a fused set of image data, and an image obtained from the fused set of image data is displayed.

The first apparatus for recording image data is preferably an apparatus with which image data for the production of high-quality images, correct in detail, from the interior of the subject can be obtained in a non-invasive manner. The second apparatus for recording image data is preferably fashioned such that images of the object that is penetrating or that has penetrated into the interior of the subject can be obtained non-invasively in an economical, simple and rapid manner. Using the first apparatus, image data are thereby obtained before the introduction of the object into the subject, and are stored. Using the second apparatus, image data are recorded, preferably in real time, during the introduction of the object into the subject, or after the object has been introduced into the subject. Finally, by producing a connection between the image data obtained using the first apparatus and the image data obtained using the second apparatus, in a registration method, and by superimposing the image data with one another, fused sets of image data are obtained from which images can be produced in real time, in which details from the interior of the subject are visible, and the object that has been introduced into the subject is visible as well. An application of the inventive method is the above-specified visualization of a biopsy needle that is penetrating or that has penetrated into the body of a living subject in a medical context. With the use of the inventive method, a movement back and forth of the living subject between two devices for recording image data during the biopsy procedure is not necessary, since image data for the visualization of the biopsy needle during the biopsy procedure are recorded using only one imaging system, and these data are fused with previously obtained image data in order to produce images that are effective in diagnosis.

The above object is also achieved in accordance with the invention in a system for visualizing the position and orientation of an object that is penetrating into a subject or that has penetrated into a subject, having a first apparatus for recording image data with which a first set of image data from the interior of the subject can be produced, a second apparatus, realized differently from the first apparatus, for recording image data with which a second set of image data from the interior of the subject can be produced, an arrangement for producing a connection between the image data of the first set and the image data of the second set, an arrangement for superposing image data of the first set with image data of the second set in order to produce a fused set of image data, and a display for graphically displaying an image obtained from the fused set of image data.

By providing an arrangement for producing a connection between image data of the first set and image data of the second set, and an arrangement for the superposition of image data, the inventive system enables the production of diagnostically effective images. During the introduction of the object into the subject it is necessary to obtain image data from the interior of the body of the subject using only one imaging system, in order to enable visualization of the position and orientation of the object in the subject. In this way, movement of the subject back and forth between first and second means for recording image data for the visualization of the object, as described above for the case of a biopsy procedure in a medical context, is avoided.

In an embodiment of the inventive system, the first apparatus is an x-ray computed tomography apparatus. The second apparatus is an x-ray apparatus having an x-ray source that emits a cone-shaped x-ray beam bundle, and a planar x-ray beam detector, in particular a C-arm x-ray apparatus, and/or an ultrasound apparatus provided with an ultrasound head, with which sets of two-dimensional and/or three-dimensional image data can be obtained. Using the x-ray computed tomography apparatus, high-resolution images, true to detail, from the interior of a subject can thereby be obtained. The C-arm x-ray apparatus and the ultrasound apparatus are distinguished in that images from the interior of a subject can be produced in real time in a simple, rapid, and economical manner.

Suitable registration methods, that can be executed by a computer for connecting the image data recorded using the first and second apparatuses are of the types known as landmark-based registration methods (cf. R. Boesecke, Th. Bruckner, G. Ende: "Landmark based correlation of medical images," Phys. Med. Biol., 1990, vol. 35, no. 1, pp. 121–126), fully automated voxel-based registration methods (cf. C. Studholme, D. L. G. Hill, D. J. Hawkes: "Automated three-dimensional registration of magnetic resonance and positron emission tomography brain images by multiresolution optimization of voxel similarity measures," United Medical and Dental Schools of Guy's and St. Thomas's Hospitals, 1996, or Colin Studholme: "Measures of 3D Medical Image Alignment, Ph.D. thesis," United Medical and Dental Schools of Guy's and St. Thomas's Hospitals, 1997), elastic registration methods (cf. Lee, Seungyong, G. Wolberg, S. Y. Shin: "Scattered Data Interpolation with Multilevel B-Splines," IEEE Transactions on Visualization and Computer Graphics, 3(3), pp.337–354,1997), or 2D, 3D registration methods (cf. G. P. Penney, J. Weese, J. A. Little, P. Desmedt, et al.: "A Comparison of Similarity Measures for Use in 2-D-3-D Medical Image Registration": IEEE Transactions on Medical Imaging, 1998, vol. 17, no. 4, pp. 586–595). In registration method of this sort, a transformation rule is determined in order to enable the image data obtained using the first apparatus and the image data obtained using the second apparatus to be superimposed with each other. In addition, the execution of a registration method is required whenever the orientation of the apparatus provided for recording image data in real time changes relative to the subject. Thus, if the projection geometry of the C-arm x-ray apparatus relative to the subject changes, or the position and/or orientation of the ultrasound head relative to the subject changes, then as a rule a new connection of the image data newly recorded using the C-arm x-ray apparatus, or the image data newly recorded using the ultrasound head, with the image data previously recorded using the x-ray computed tomography apparatus must take place in the form of a registration procedure.

In a preferred specific embodiment of the invention the second apparatus is an ultrasound apparatus, and a position acquisition system is used with which the position of the ultrasound head of the ultrasound apparatus can be continuously acquired. In this way, a registration method for connecting image data obtained using the x-ray computed tomography apparatus and the ultrasound image data need to be carried out only once, at the beginning of a visualization procedure, because with the aid of the position acquisition system, position changes of the set of ultrasound image data, recorded using the ultrasound apparatus, relative to the subject are continuously determined, and the connection with the image data recorded using the x-ray computed tomography apparatus can be adapted corresponding to the current position of the ultrasound head.

DESCRIPTION OF THE PREFERRED EMBODIMENTS

Figure 1:
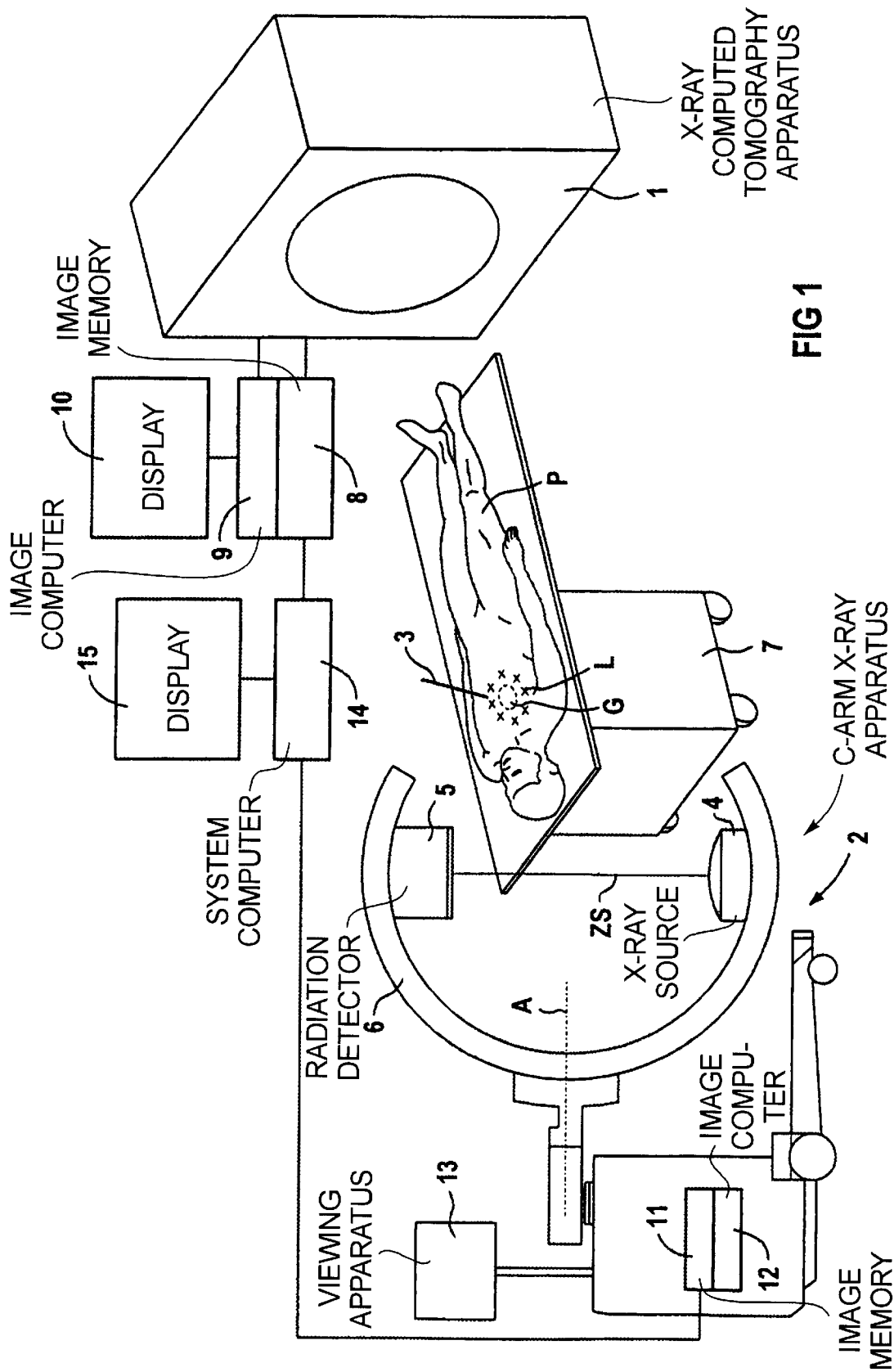
FIG. 1 shows a system with an x-ray computed tomography apparatus and a C-arm x-ray apparatus, constructed and operating in accordance with the invention.

In FIG. 1, a first exemplary embodiment of the invention is shown as a medical system with an x-ray computed tomography apparatus 1 and a C-arm x-ray apparatus 2, with which the inventive method can be executed. In the exemplary embodiment, the method is for visualizing the position and orientation of a biopsy needle 3 during a biopsy procedure that is to be carried out on a patient P. The x-ray computed tomography apparatus 1 and the C-arm x-ray apparatus 2 are realized in a known way. The C-arm 6 of the x-ray apparatus 2, provided with an x-ray source 4 and an x-ray detector 5, is height-adjustable, and can be adjusted along its circumference (orbital motion), and can be pivoted around an axis A that proceeds horizontally (angulation).

In the exemplary embodiment, the patient P is positioned on a movable patient bed 7, and has tissue G that is of interest in the interior of his body, from which a tissue sample is to be taken using the biopsy needle 3.

In order to enable representation of the position and orientation of the biopsy needle 3 relative to the tissue G in images, to aid a physician (not shown in FIG. 1) conducting the biopsy procedure, in a first step, without the biopsy needle 3 being introduced into the patient P, the x-ray computed tomography apparatus 1 is used in a known way to obtain a set of 3D image data from the body region of the patient P containing the tissue G, and this set of data is intermediately stored in an image memory 8. From the set of 3D image data, an image computer 9 of the x-ray computed tomography apparatus 1 can be used in a known way to reconstruct images showing the tissue G, and to display them on a display 10 as tomograms in the form of a 3D visualization. On the basis of the images, the tissue G can be marked interactively in the set of 3D image data, using input means (not shown in FIG. 1) that are connected to the image computer 9, for example a joystick, a trackball, or a mouse, for additional simplified identification.

Following the recording of the image data using the x-ray computed tomography apparatus 1, the execution of the biopsy procedure takes place with x-ray monitoring using the C-arm x-ray apparatus 2. During the penetration of the biopsy needle 3 into the body of the patient P, or after the penetration of the biopsy needle 3 into the body of the patient P, sets of 2D image data are recorded using the C-arm x-ray apparatus 2 from at least two different projection directions, i.e., with different positioning of the C-arm 6 relative to the patient P, and are intermediately stored in an image memory 11 of the C-arm x-ray apparatus 2. Preferably, two sets of 2D image data are recorded from two projection directions that are orthogonal to one another, in order to enable representation of the position, the orientation, and also, if warranted, deformations, for example bending, of the biopsy needle 3, and also its depth of penetration into the body or the tissue G. From the sets of 2D image data, using an image computer 12 of the C-arm x-ray apparatus 2, 2D images from the interior of the body of the patient P can be reconstructed and displayed on a viewing apparatus 13 of the C-arm x-ray apparatus 2.

In the exemplary embodiment, the image memory 8 of the x-ray computed tomography apparatus 1 and the image memory 11 of the C-arm x-ray apparatus 2 are connected to a system computer 14 which can access the set of 3D image data obtained using the x-ray computed tomography apparatus 1 and the sets of 2D image data obtained using the C-arm x-ray apparatus 2. Upon request, for example by the physician, or continuously with the aid of registration methods, the system computer 14 produces a connection between the set of 3D image data of the x-ray computed tomography apparatus 1 and the sets of 2D image data of the C-arm x-ray apparatus 2. If, as in the case of the exemplary embodiment, the patient P is provided with landmarks L, which can be imaged in x-ray exposures and are indicated schematically in FIG. 1, the connection between the set of 3D image data and the sets of 2D image data can be produced on the basis of a landmark-based registration method, since the landmarks L can be identified both in the set of 3D image data and in the sets of 2D image data. After a connection of this sort of the set of 3D image data with the sets of 2D image data, the system computer 14 can superimpose image data of the set of 3D image data with image data of one of the sets of 2D image data, and thus can produce fused sets of image data, from which, in turn, images that can be displayed on a display 15 can be reconstructed. In the exemplary embodiment, the system computer 14 superimposes each of the (at least) two sets of 2D image data, obtained using the C-arm x-ray apparatus 2, with the set of 3D image data obtained using the x-ray computed tomography apparatus 1. The images produced from the superposed image data show, in a three-dimensional view, the position, orientation, shape, and depth of penetration of the biopsy needle 3 relative to the tissue G that is to be examined and that is interactively marked. In order to assist the physician conducting the biopsy procedure with images, the inventive system and the inventive method combine the advantages of x-ray computed tomography with the advantages of a C-arm x-ray system, but with a repositioning of the patient P, or movement of the patient P, between different imaging modalities during the biopsy procedure no longer being required.

As an alternative to a landmark-based registration method for connecting the set of 3D image data with the sets of 2D image data, a fully automatic voxel-based registration method for this 2D, 3D registration can be used, in which gray values in the image data are checked for maximal agreement.

If, for example, patient movements, patient repositionings, breathing, or the like result in differences with respect to the anatomical imaging of tissue structures of the patient P in the set of 3D image data and in the sets of 2D image data, elastic registration methods for 2D, 3D registration can be used.

A further possibility for fusing image data in order to achieve diagnostically effective image information for the physician carrying out the biopsy procedure is the fusing of projections known as maximum intensity projections, produced from the set of 3D image data, with a respective set of 2D image data obtained using the C-arm x-ray device 2. A maximum intensity projection is obtained by applying a set of parallel straight lines through the set of 3D image data at an angle that can be selected arbitrarily, whereby along each individual straight line the point having the highest signal intensity is sought and is projected into the plane that is perpendicular to the straight lines. In this way, there arises a projected set of 2D image data, which is called a maximum intensity projection.

After connection of a first set of 2D image data with the set of 3D image data by carrying out a suitable registration method, the system computer 14 produces a first maximum intensity projection from the set of 3D image data using the same spatial orientation with which the first set of 2D image data was obtained using the C-arm x-ray apparatus 2. That is, the first maximum intensity projection is produced from the set of 3D image data in the spatial direction that substantially corresponds to the spatial direction of the central beam ZS of an x-ray beam bundle of the C-arm x-ray apparatus 2, that proceeds from the x-ray source 4 to the x-ray beam detector 5, during the recording of the first set of 2D image data. Analogously, after the connection of a second set of 2D image data with the set of 3D image data, the production of a second maximum intensity projection takes place in the same spatial direction corresponding to the spatial direction of the central beam ZS of the C-arm x-ray apparatus 2 during the recording of the second set of 2D image data.

Following this, the system computer 14 superimposes the 2D image data of the first maximum intensity projections with the first set of 2D image data, and superposes the 2D image data of the second maximum intensity projections with the second set of 2D image data to form fused sets of image data from which diagnostically effective images showing the position, orientation, shape, and depth of penetration of the biopsy needle 3 relative to the tissue G can be produced in order to aid the biopsy procedure, which are displayed on the display 15.

Any type of x-ray computed tomography apparatus can be used to record the sets of 3D image data before the biopsy procedure.

The inventive method can also be used in sliding gantry apparatuses, whereby no movement of the patient P during the biopsy procedure is required.

Figure 2:
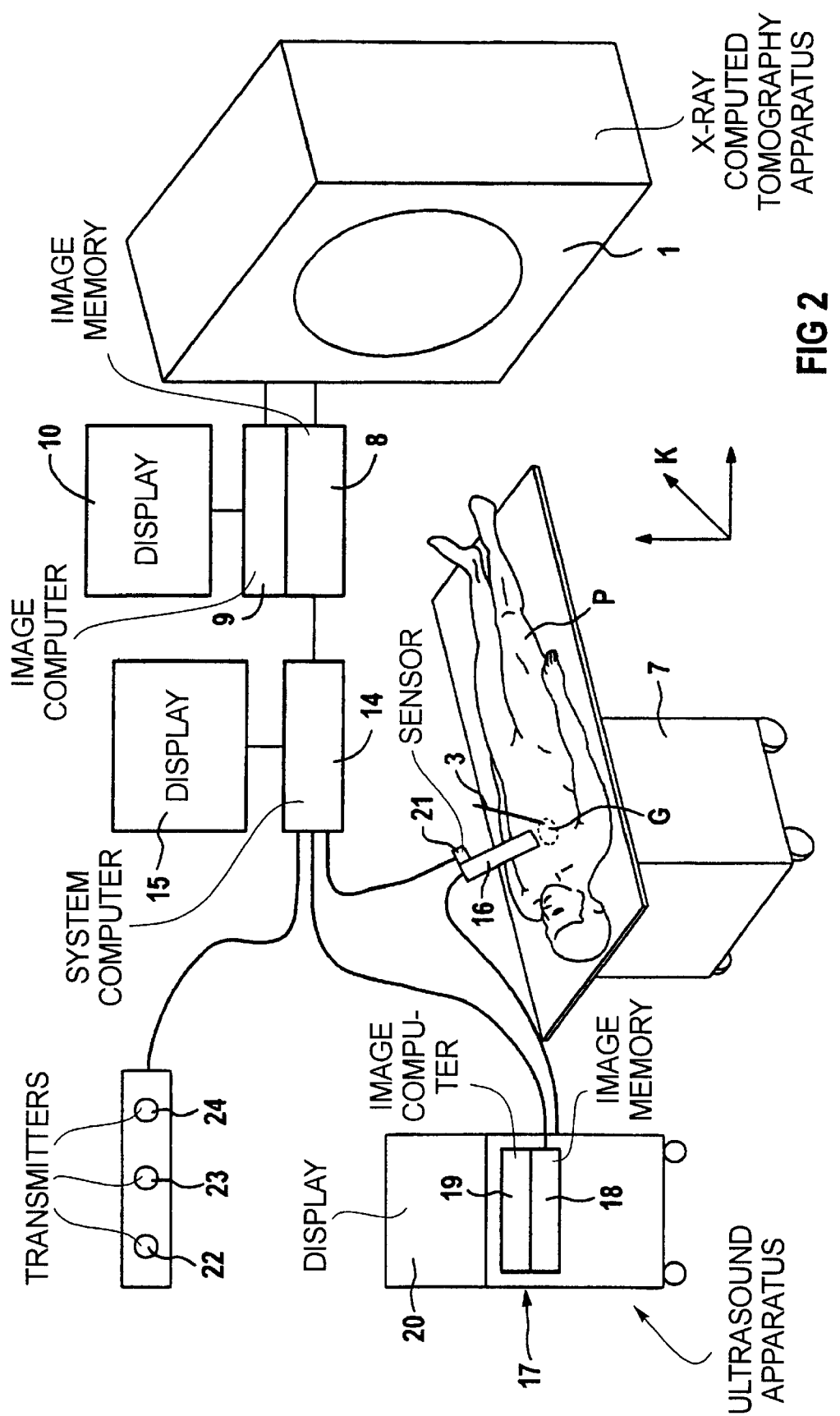
FIG. 2 shows a system with an x-ray computed tomography apparatus and an ultrasound apparatus constructed and operating in accordance with the invention.

FIG. 2 shows a second exemplary embodiment of an inventive system with which the inventive method—in the present case, the method for visualizing the position and orientation of a biopsy needle 3 that is penetrating or has penetrated into the body of a patient P—can likewise be carried out. Components of the system shown in FIG. 2 that are substantially identical in design and function to components of the system shown in FIG. 1 are provided with identical reference characters. In contrast to the exemplary embodiment shown in FIG. 1, the exemplary embodiment shown in FIG. 2 does not have a C-arm x-ray apparatus 2, but rather has an ultrasound apparatus 17, provided with an ultrasound head 16, for obtaining sets of image data.

Using the ultrasound apparatus 17, sets of 2D and/or 3D image data from the interior of the body of the patient P can be obtained in a known way using various orientations of ultrasound head 16 relative to the body surface of the patient P.

As in the case of the first exemplary embodiment, in a first step a set of 3D image data of the bodily region of the patient P including the tissue G that is to be examined is obtained, using the x-ray computed tomography apparatus 1 without introduction of the biopsy needle 3, and is stored in the image memory 8, to which the system computer 14 has access.

Subsequently, using the ultrasound head 16, which in a known manner (not shown) includes ultrasound transmission and reception transducers, sets of 2D or 3D ultrasound image data are recorded in real-time by the ultrasound apparatus 17 without spatial limitation during the introduction of the biopsy needle 3 into the body of the patient P or given a biopsy needle 3 introduced into the body, and these sets of data are stored in an image memory 18 of the ultrasound apparatus 17. Using an image computer 19 of the ultrasound apparatus 17, images that can be represented on a display 20 of the ultrasound apparatus 17 can be produced. The system computer 14 has access to the obtained sets of 2D or 3D ultrasound image data.

As in the manner described above, by executing known 2D/3D, or 3D/3D, registration methods, the system computer 14 connects each desired set of 2D or 3D ultrasound image data with the set of 3D image data obtained using the x-ray computed tomography apparatus 1. After connection of the sets of image data, the system computer 14 can in turn carry out a superposition of image data of the set of 3D image data obtained using the x-ray computed tomography apparatus 1 with each set of 2D or 3D ultrasound image data, and can produce therefrom images that can be displayed on the display 15 that provide anatomical information showing the position, orientation, shape, and depth of penetration of the biopsy needle 3 relative to the tissue G in real time.

Since, during the recording of sets of 2D or 3D ultrasound image data, a change in the position or orientation of the ultrasound head 16 relative to the patient P always requires a new execution of a registration method for connecting the newly recorded sets of 2D or 3D ultrasound image data with the set of 3D image data recorded using the x-ray computed tomography apparatus 1, in the second exemplary embodiment the system including the ultrasound apparatus 17 has a position acquisition system.

In the second exemplary embodiment, the position acquisition system includes three transmitters 22 to 24 for electromagnetic waves, and a sensor 21 that can be attached to the ultrasound head 16 in a defined manner. The sensor 21 receives the electromagnetic waves transmitted by the transmitters 22 to 24. The sensor 21 and the transmitters 22 to 24 are connected to the system computer 14. The electromagnetic waves transmitted by the transmitters 22 to 24 during operation of the position acquisition system are registered by the sensor 21 and are evaluated by the system computer 14 in order to determine the position of the ultrasound head 17 in a reference coordinate system K defined by the system computer 14. The position of the transmitters 22 to 24 in the reference coordinate system K is known to the system computer 14. The system computer 14 accordingly always can determine the position and orientation of the ultrasound head 16, and thus the position and orientation of a set of ultrasound image data recorded using the ultrasound head 16, in the reference coordinate system K, on the basis of phase and transit-time measurements of the electromagnetic waves, due to the defined attachment of the sensor 21 to the ultrasound head 16. This means that the registration method, in the event of positional changes of the ultrasound head 16, need not be executed constantly under real-time demands, which is advantageous because the registration method is computation-time intensive. Rather, a registration method need be executed only once, at the beginning of the visualization method, with a connection created between the set of 3D image data obtained using the x-ray computed tomography apparatus 1, whose position (i.e., the position of the set of data) in the reference coordinate system K can likewise be determined by the system computer 14, and a set of ultrasound image data. Subsequently, changes in position relative to the patient P of sets of ultrasound image data obtained using the ultrasound head 16 can be determined continuously with the aid of the position acquisition system, and the connection of newly obtained sets of 2D or 3D ultrasound image data with the set of 3D image data of the x-ray computed tomography apparatus 1 can be adapted correspondingly.

According to the inventive method, a first set of 3D image data is thus obtained using an x-ray computed tomography apparatus 1. During the biopsy procedure, sets of 2D or 3D image data are obtained using a C-arm x-ray apparatus 2 and/or using an ultrasound apparatus 17, and are fused, continuously or as needed, with the set of 3D image data obtained using the x-ray computed tomography apparatus 1.

In this way, images can be produced that show the position, orientation, shape, and depth of penetration of the biopsy needle 3 relative to the tissue G that is to be examined. The recording of the sets of image data using the C-arm x-ray apparatus 2 or using the ultrasound apparatus 17, the connection of the sets of image data with the set of 3D image data obtained using the x-ray computed tomography apparatus 1, the superimposition of the image data, and the production and displaying of the images can thereby take place in real time.

The above-described exemplary embodiments are presented only as examples. In particular, components of the specified systems for the execution of the method can be replaced by other components that have the same functionality. Thus, for example, the electromagnetic position acquisition system can be replaced by an optical position acquisition system. Mixed forms of the exemplary embodiments are also possible, i.e., the system for the execution of the inventive method can be both a C-arm x-ray apparatus and also an ultrasound apparatus.

In principle, there is also the possibility of using the C-arm x-ray apparatus to obtain sets of 3D image data, and to connect these sets with the sets of 3D image data obtained using the x-ray computed tomography apparatus 1.

Instead of an x-ray computed tomography apparatus, a magnetic resonance imaging apparatus can be used for the acquisition of sets of 3D image data.

The application of the inventive method is not limited to the field of medicine. In this sense, the inventive system need not necessarily be a medical system.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for visualizing a position and orientation of an object at least partially disposed in an interior of an examination subject, comprising the steps of:
   (a) producing a first set of image data from said interior of said subject using a first apparatus for recording image data, before said object is disposed in said interior;
   (b) producing a second set of image data from said interior of said subject using a second apparatus for recording image data, realized differently from said first apparatus for recording image data, at a time when at least a portion of said object is disposed in the interior of the subject;
   (c) producing a linkage between said image data of said first set and said image data of said second set;
   (d) dependent on said linkage, superimposing said image data of said first set with said image data of said second set to form a fused set of image data; and
   (e) producing a fusion image from said fused set of image data and displaying said fusion image obtained from the fused set of image data.

2. A method as claimed in claim 1 wherein step (a) comprises producing said first set of image data using an imaging apparatus for obtaining 3D image data as said first set of image data.

3. A method as claimed in claim 2 comprising producing said first set of image data with an imaging modality selected from the group consisting of a computed tomography apparatus and a magnetic resonance imaging apparatus.

4. A method as claimed in claim 1 wherein step (b) comprises producing said second set of image data using an apparatus for obtaining sets of 2D image data as said second set of image data.

5. A method as claimed in claim 4 comprising producing said second set of image data with an x-ray apparatus by irradiating said subject with x-rays from different projection directions to respectively obtain said sets of 2D image data.

6. A method as claimed in claim 5 wherein step (a) comprises producing said first set of image data using an apparatus for producing 3D image data as said first set of image data and wherein step (d) comprises superimposing at least two of said sets of 2D image data in said second set of image data with said 3D image data in said first set of image data.

7. A method as claimed in claim 1 wherein step (b) comprises producing said second set of image data with an x-ray apparatus which irradiates said examination subject from different projection directions to obtain a plurality of sets of 2D image data, and wherein a first of said sets of 2D image data has a first spatial orientation and a second of said sets of 2D image data has a second spatial orientation, and wherein step (a) comprises producing said first set of image data using an x-ray computed tomography apparatus to produce a set of 3D image data, as said first set of image data, and wherein step (a) further comprises producing a first maximum intensity projection from said set of 3D image data from said first spatial orientation and producing a second maximum intensity projection from said set of 3D image data from said second spatial orientation, and wherein step (d) comprises superimposing said first maximum intensity projection with said first of said sets of 2D image data and superimposing said second maximum intensity projection with said second of said sets of 2D image data.

8. A method as claimed in claim 1 wherein step (b) comprising producing said second set of image data using an ultrasound imaging system.

9. A method as claimed in claim 8 wherein said ultrasound imaging system includes an ultrasound head, and further comprising identifying a position of said ultrasound head using a position acquisition system.

10. A method as claimed in claim 8 comprising producing a set of 2D ultrasound image data, as said second data set, using said ultrasound imaging apparatus.

11. A method as claimed in claim 8 comprising producing a set of 3D ultrasound image data, as said second data set, using said ultrasound imaging apparatus.

12. A system for visualizing a position and orientation of an object at least partially disposed in an interior of an examination subject, comprising:
   a first apparatus for recording image data for producing a first set of image data from said interior of said subject before an object is disposed in said interior;
   a second apparatus for recording image data, different from said first apparatus for recording image data, for producing a second set of image data from said interior of said subject after an object is at least partially disposed in said interior;
   an arrangement for producing a linkage between the image data of said first set and the image data of said second set;
   an arrangement for superimposing said image data of said first set with said image data of said second, dependent on said linkage, set to produce a fused set of image data; and
   an arrangement for producing an fusion image from said first set of image data and for displaying said fusion image from said fused set of image data.

13. A system as claimed in claim 12 wherein said first apparatus for recording image data is an x-ray computed tomography apparatus.

14. A system as claimed in claim 12 wherein said second apparatus for recording image data is an x-ray apparatus.

15. A system as claimed in claim 12 wherein said second apparatus for recording image data is an ultrasound apparatus.

16. A system as claimed in claim 15 wherein said ultrasound apparatus has an ultrasound head, and further comprising a position acquisition system for identifying a position of said ultrasound head.

17. A system as claimed in claim 16 wherein said position acquisition system includes a sensor attached to said ultrasound head.

18. A system as claimed in claim 12 wherein said arrangement for producing said connection between the image data of said first set and the image data of the second set is a computer.

19. A system as claimed in claim 12 wherein said arrangement for producing said connection between the image data of said first set and the image data of said second set includes marks adapted for attachment to said subject which are registerable using each of said first apparatus for recording image data and said second apparatus for recording image data.

20. A system as claimed in claim 12 wherein said first apparatus is an apparatus for recording 3D image data as said first set of image data, and wherein said second apparatus is an apparatus for recording 2D image data as said second set of image data.

21. A system as claimed in claim 20 wherein said first apparatus is an imaging apparatus selected from the group consisting of a computed tomography apparatus and a magnetic resonance imaging apparatus, and wherein said second apparatus is an apparatus selected from the group consisting of an ultrasound imaging apparatus and an X-ray imaging apparatus.

* * * * *